(12) United States Patent
Pauley et al.

(10) Patent No.: US 7,387,622 B1
(45) Date of Patent: Jun. 17, 2008

(54) RAPID EXPANSION TAMPON PLEDGET

(75) Inventors: Suzanne M. Pauley, Dover, DE (US);
Jeffrey M. Brown, Ramsey, NJ (US);
Irwin Butensky, Teaneck, NJ (US);
Dane R. Jackson, Bloomingdale, NJ (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/414,764

(22) Filed: Oct. 7, 1999

(51) Int. Cl.
*A61F 13/15* (2006.01)
*A61F 13/20* (2006.01)

(52) U.S. Cl. .................... 604/385.18; 604/904

(58) Field of Classification Search .............. 604/367, 604/385.18, 904, 385.17, 368
See application file for complete search history.

(56) References Cited

U.S. PATENT DOCUMENTS

| | | | |
|---|---|---|---|
| 1,884,089 A | 10/1932 | Millner | |
| 2,330,257 A | 9/1943 | Bailey | |
| 2,391,343 A | 12/1945 | Popper | |
| 2,499,414 A | 3/1950 | Rabell | |
| 2,761,449 A | 9/1956 | Bletzinger | 128/285 |
| 2,884,925 A | 5/1959 | Meynier, Jr. | |
| 3,369,544 A | 2/1968 | Crockford | 128/285 |
| 3,431,909 A | 3/1969 | Krusko | |
| 3,674,025 A | 7/1972 | Bleuer | |
| 3,706,311 A | 12/1972 | Kokx et al. | |
| 3,731,687 A | 5/1973 | Glassman | |
| 3,749,094 A | 7/1973 | Duncan | |
| 3,762,413 A | 10/1973 | Hanke | |
| 3,815,601 A | 6/1974 | Schaefer | |
| 3,834,389 A | 9/1974 | Dulle | |
| 3,986,511 A | 10/1976 | Olofsson et al. | |
| 4,018,225 A | 4/1977 | Elmi | |
| 4,020,841 A | 5/1977 | Poncy et al. | 128/285 |
| 4,200,101 A | 4/1980 | Glassman | |
| 4,211,225 A | 7/1980 | Sibalis | |
| 4,212,301 A | 7/1980 | Johnson | |
| 4,216,772 A | 8/1980 | Tsuchiya | |
| 4,266,546 A | 5/1981 | Roland et al. | |
| 4,300,561 A | 11/1981 | Kaczmarzyk et al. | 128/285 |
| 4,335,721 A * | 6/1982 | Matthews | |
| 4,377,615 A | 3/1983 | Suzuki et al. | |
| 4,475,911 A | 10/1984 | Gellert | |
| 4,543,098 A | 9/1985 | Wolfe et al. | 604/370 |
| 4,675,217 A | 6/1987 | Forsman | |
| 4,787,895 A | 11/1988 | Stokes et al. | 604/358 |
| 5,006,116 A * | 4/1991 | Alikhan et al. | |
| 5,231,122 A | 7/1993 | Palumbo et al. | |
| 5,364,383 A | 11/1994 | Hayes et al. | |
| 5,374,258 A * | 12/1994 | Lloyd et al. | |

(Continued)

FOREIGN PATENT DOCUMENTS

EP    0 062 948    10/1982

OTHER PUBLICATIONS

European Search Report, dated Jul. 22, 2004.

*Primary Examiner*—Michele Kidwell
(74) *Attorney, Agent, or Firm*—Ohlandt, Greeley, Ruggiero & Perle, L.L.P.

(57) ABSTRACT

There is provided a tampon pledget that expands without the aid of moisture or menses. The tampon pledget has a plurality of high resiliency, non-absorbent fibers and a plurality of absorbent fibers. The tampon pledget has improved comfort as compared to conventional fully compressed tampon pledgets.

11 Claims, 1 Drawing Sheet

U.S. PATENT DOCUMENTS

Figure 1:
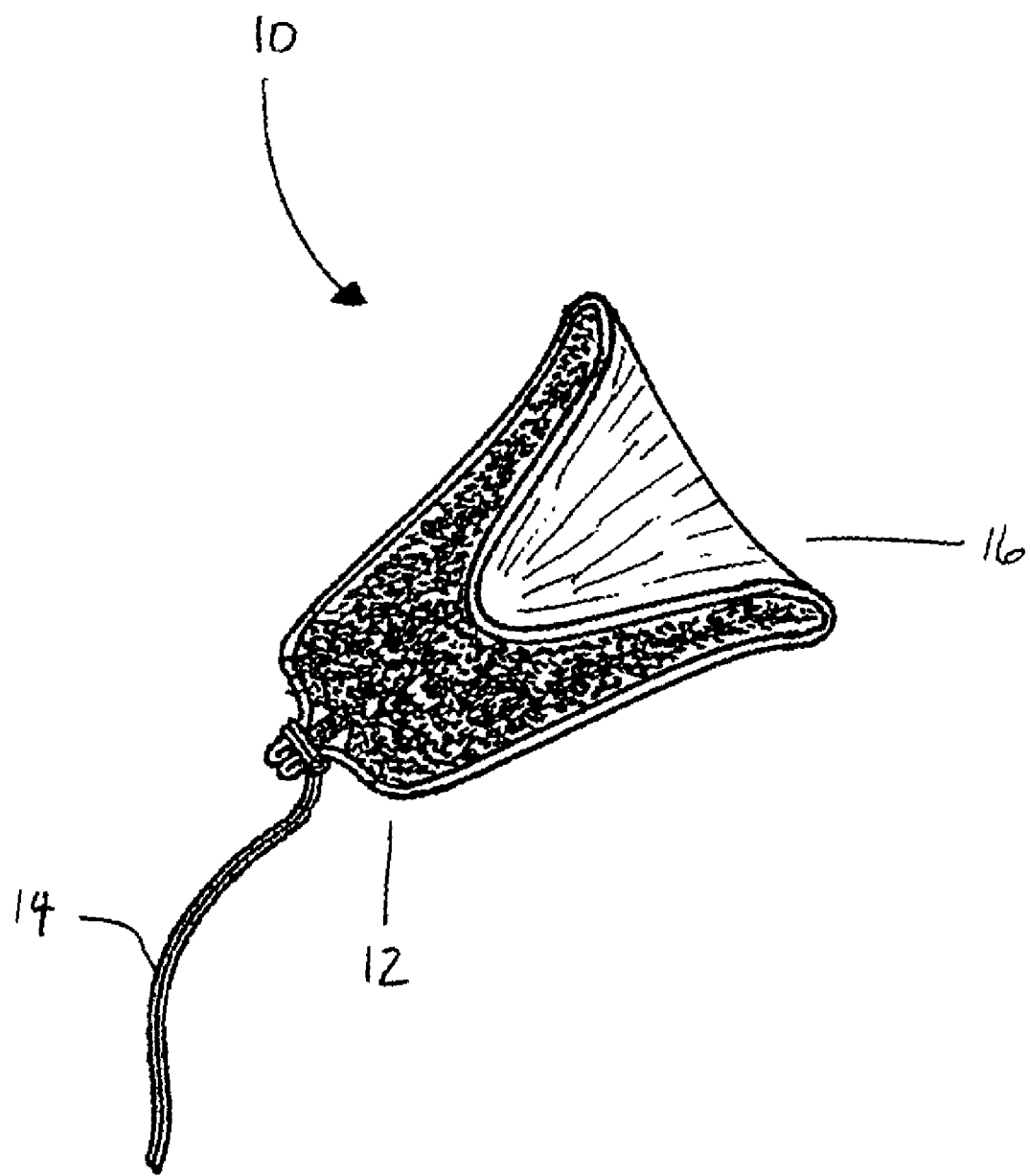

| | | |
|---|---|---|
| 5,476,455 A | 12/1995 | Silber |
| 5,542,914 A | 8/1996 | Van Iten |
| 5,566,435 A | 10/1996 | Brown, Jr. |
| 5,659,934 A | 8/1997 | Jessup et al. |
| 5,755,906 A | 5/1998 | Achter et al. |
| 5,795,346 A | 8/1998 | Achter et al. |
| 5,817,077 A * | 10/1998 | Foley et al. |
| 5,928,184 A | 7/1999 | Etheredge et al. ............. 604/15 |

* cited by examiner

RAPID EXPANSION TAMPON PLEDGET

BACKGROUND OF THE INVENTION

1. Field of the Invention

The present invention relates generally to an improved tampon or tampon pledget. More particularly, the present invention relates to a tampon pledget that expands rapidly when ejected from a tampon applicator, without the need for the tampon pledget contacting moisture or menses. Furthermore, the tampon pledget has improved comfort and good absorbency.

2. Description of the Prior Art

Tampon pledgets are typically compressed and set during either manufacture or placement of the pledget in a tampon applicator prior to use. In conventional tampon pledgets, the pledget's fibers will expand significantly upon initial contact with moisture, or menses once placed in a user's body. During expansion, the tampon pledget would conform to the user's body contours. Heretofore, it was thought that the tampon pledget needed to be ejected from the applicator and positioned within the user's body before expansion in order to achieve comfort.

Non-absorbent fibers have been used in a tampon pledget to provide expansion to the pledget. However, such tampon pledgets have not achieved the unexpected comfort of the tampon pledget of the present invention. Frankly, one would not think to improved comfort, and have comparable absorbency and sufficient bypass leakage protection, in a tampon pledget by combining non-absorbent and absorbent fibers. In addition, there has been a lack of appreciation that the correct ratio of non-absorbent fibers to absorbent fibers, including conventional absorbent fibers, provides improved comfort, and absorbency that is as good or better than known tampon pledgets.

SUMMARY OF THE INVENTION

It is an object of the present invention to provide a tampon pledget that expands rapidly when dry.

It is another object of the present invention to provide such a tampon pledget that has improved comfort, and comparable or better absorbency, than known tampon pledgets.

It is a further object of the present invention to provide such a tampon pledget that has a plurality of non-absorbent fibers and a plurality of absorbent fibers.

It is still a further object of the present invention to provide such a tampon pledget in which the plurality of non-absorbent and absorbent fibers are distributed together in the pledget, or blended together in a certain percent ratio.

It is yet a further object of the present invention to provide such a tampon pledget that may have a coverstock.

These and other objects of the present invention will be appreciated from a tampon pledget that will expand when dry. The pledget comprises a plurality of non-absorbent fibers, and a plurality of absorbent fibers that are distributed or mixed with the plurality of absorbent fibers. The tampon pledget preferably has all of its fibers enclosed in a coverstock.

The plurality of non-absorbent fibers are made of high resiliency fibers. The plurality of absorbent fibers are made of cellulosic fibers.

FIG. 1 is a side view of a bell-shaped tampon pledget according to the present invention.

DETAILED DESCRIPTION OF THE INVENTION

The tampon pledget of the present invention is called a dry expansion or fast blooming tampon pledget. The expansion of the tampon pledget is immediate upon release from a tampon applicator so that the expansion occurs entirely or primarily in its dry state. Thus, moisture or menses is not needed to expand the tampon pledget.

The expansion of the tampon pledget of the present invention in its dry state occurs faster than the expansion of a conventional or known, fully compressed tampon pledgets when in contact with moisture or menses. Basically, the latter requires contact with moisture or menses to cause the fibers of the tampon pledget to expand, while the former occurs immediately upon ejection from the tampon applicator due to the nature of the non-absorbent fibers and the percent ratio of non-absorbent to absorbent fibers in the tampon pledget. It is preferred that the non-absorbent fibers have a wet modulus, measured at 5% extension, of about 10 gram/denier to about 60 gram/denier.

With such expansion immediately upon insertion into a user's body, it has unexpectedly been found that the tampon pledget of the present invention has improved comfort.

The length of the tampon pledget of the present invention is approximately the same length as a conventional or known tampon pledget, namely about two inches. Prior to expansion, the diameter of the present tampon pledget is also approximately the same as that of conventional tampon pledgets. However, the tampon pledget of the present invention, having the same length and initial diameter of such conventional tampon pledgets, expands on its own volition when ejected from the tampon applicator and before moisture is absorbed into the tampon pledget. The expansion of the tampon pledget is to a diameter larger than that of such comparable, conventional tampon pledgets. Thus, just prior to contact with the menses of the vagina, this tampon pledget has expanded into place.

The tampon pledget of the present invention is a combination of a plurality of non-absorbent fibers and a plurality of absorbent fibers.

In a preferred embodiment, the absorbent fibers and non-absorbent fibers are distributed together. The distribution could be a blending or mixing. The blending could be either randomly or as desired.

The distribution could also be by layers. For example, the non-absorbent fibers can be one layer sandwiched between two layers of absorbent fibers. Alternatively, there can be two layers with one layer being non-absorbent fibers and the other layer being absorbent fibers.

In an alternative, less preferred embodiment, the non-absorbent fibers are the core of the tampon pledget. The non-absorbent fibers are basically surrounded by the absorbent fibers.

The non-absorbent fibers urge the absorbent fibers outward from the center of the tampon pledget. Thus, the non-absorbent fibers are selected to provide high wet resiliency or springiness to the absorbent structures of the tampon pledget. Thus, the non-absorbent fibers are preferably curly, crimped or springy fibers.

Such non-absorbent fibers are polyester, polypropylene, polyethylene, aramid, nylon, acrylic or bicomponent fibers. The polyester fibers are sold by Fiber Innovation Technology, Inc. under the tradename 4DG fibers. The 4DG fibers have a unique crenulated cross-section which results in deep grooves or channels along the longitudinal axis of the fibers. Preferably, the non-absorbent fibers are polyester or 4DG fibers.

The non-absorbent fibers may, preferably, have a hydrophilic finish. It is preferred that the non-absorbent fibers are about 0.75 to about 30 denier fibers. More preferably, the non-absorbent fibers are 15 denier.

The absorbent fibers can be any cellulosic fiber, such as, for example, rayon, lyocell, wood pulp, cotton, or superabsorbent, such as, for example, polyacrylate. The preferred absorbent fibers are rayon, superabsorbent or a combination of both fibers. The absorbent fibers are about 0.75 to about 30 denier. Preferably, the rayon fibers are about 1.5 denier and the superabsorbent fibers are about 9 denier.

In a more preferred tampon pledget of the present invention, the tampon pledget is made of 4DG non-absorbent fibers, and a combination of rayon and superabsorbent, absorbent fibers.

The ratio of non-absorbent fibers to absorbent fibers is significant. In the more preferred embodiment, the ratio of the rayon and superabsorbent fibers appears significant to improve comfort further and performance over the selection of just one type of absorbent fiber.

It has been found that for optimum expansion and absorbency, the percent ratio of non-absorbent fibers to absorbent fibers is about 25/75 to about 65/35. In the more preferred embodiment, the ratio of rayon to superabsorbent fibers is about 70/30. Thus, the more preferred tampon pledget of the present invention, namely Eastman 4DG, rayon and superabsorbent (such as polyacrylate), the percent ratio of non-absorbent/rayon/superabsorbent fibers is about 35/46/19.

The tampon pledget of the present invention has its insertion end recessed into the center of the pledget, and is crimped or compressed to a certain extent for insertion into a tampon applicator. The compression should be just enough so that the tampon pledget is "spring-loaded" in the tampon applicator. Once ejected from the tampon applicator, the tampon pledget will expand rapidly preferably into a bell-like shape configuration, as represented generally by reference numeral 10 in FIG. 1. The tip or top 12 of this bell-shaped pledget 10 has the removal string 14 secured to it, while the other end of the tampon pledget 10 forms the base 16 of the bell.

Immediately after ejection from the tampon applicator (and before contact with menses), this tampon pledget has a free diameter at its widest point from about 25% to about 300% larger than just prior to ejection. Preferably, the tampon pledget has, immediately after ejection from the tampon applicator, a free diameter at its widest point about 225% larger than just prior to ejection.

The tampon pledget can also expand into a cylindrical shape, instead of a bell-shape if the insertion end is not initially tucked in.

The tampon pledget is preferably within a coverstock that encloses, preferably fully encloses, an amorphous blend of non-absorbent and absorbent fibers. The coverstock can be any conventional coverstock. However, the coverstock is preferably a non-woven, heat sealable coverstock, such as, for example, polyethylene/polypropylene bicomponent spunbonded coverstock.

By the inherent rapid, dry expansion of the tampon pledget of the present invention, the tampon pledget conforms during insertion more quickly to the user. Also, there is no need for moisture to contact the tampon pledget and be absorbed into the pledget to cause the expansion. The fact that the tampon pledget more quickly conforms to the user apparently results in the improved comfort.

The present tampon pledget having non-absorbent fibers, and especially the percent ratio of non-absorbent to absorbent fibers, has unexpectedly been found to achieve this improved comfort without loss of absorbency. For example, in a 102 women actual use test, 47% of the women preferred the tampon pledget of the present invention for "being comfortable to wear", as compared to just 26% for the Kotex® Security® super tampon.

The tampon pledget of the present invention has also been found to have absorbency about equal to or better than known tampon pledgets. A syngyna test was conducted pursuant to FDA specified test method, reference 21 CFR 801.430. The following is a table of the results of a syngyna test conducted in a laboratory. All tested tampons had a super absorbency classification.

| TAMPON TYPE | SYNGYNA ABSORBENCY (in grams) |
|---|---|
| Present pledget | 10.9 |
| Kotex ® Security ® | 11.2 |
| Playtex ® Silk Glide ® | 10.4 |
| Playtex ® Gentle Glide ® | 10.1 |
| Tampax ® | 9.7 |

Various modifications to the present invention may be made as will be apparent to those skilled in the art. Thus, it will be obvious to one of ordinary skill in the art that the foregoing description is merely illustrative of certain preferred embodiments of the present invention.

What is claimed is:

1. A dry expanding tampon pledget comprising:
    a plurality of non-absorbent fibers; and
    a plurality of absorbent fibers, wherein said plurality of absorbent fibers is a combination of rayon fiber and superabsorbent fiber, and wherein a ratio of rayon fiber to superabsorbent fiber is about 70/30,
    wherein said plurality of non-absorbent fibers and said plurality of absorbent fibers are blended together to form the dry expanding tampon pledget, and
    wherein immediately after complete ejection from an applicator, and prior to contact with menses, the dry expanding tampon pledget has a free diameter at a widest point from about 25% to about 300% larger than a diameter at said widest point of the dry expanding tampon pledget in the applicator.

2. The tampon pledget of claim 1, wherein a percent ratio of said plurality of non-absorbent fibers to said plurality of absorbent fibers is about 25/75 to about 65/35.

3. The tampon pledget of claim 1, wherein said plurality of non-absorbent fibers are selected from the group consisting of polyester, polypropylene, polyethylene, aramid, nylon, acrylic, bicomponent, and mixtures thereof.

4. The tampon pledget of claim 1, wherein said plurality of non-absorbent fibers are polyester fibers.

5. The tampon pledget of claim 1, wherein said plurality of non-absorbent fibers are about 0.75 to about 30 denier.

6. The tampon pledget of claim 1, wherein the plurality of absorbent fibers are about 0.75 to about 30 denier.

7. The tampon pledget of claim 1, further comprising a coverstock.

8. A dry expanding tampon pledget comprising:
    a plurality of non-absorbent fibers; and
    a plurality of absorbent fibers, wherein said plurality of absorbent fibers is a combination of rayon fiber and superabsorbent fiber,
    wherein said plurality of non-absorbent fibers and said plurality of absorbent fibers are blended together to form the dry expanding tampon pledget,
    wherein a percent ratio of said plurality of non-absorbent fibers to said plurality of absorbent fibers is about 25/75 to about 65/35, and
    wherein immediately after complete ejection from an applicator, and prior to contact with menses, the dry expanding tampon pledget has a free diameter at a widest point from about 25% to about 300% larger than a diameter at said widest point of the dry expanding tampon pledget in the applicator.

9. A dry expanding tampon pledget comprising:

a plurality of non-absorbent fibers, wherein said plurality of non-absorbent fibers are selected from the group consisting of polyester, polypropylene, polyethylene, aramid, nylon, acrylic, bicomponent, and mixtures thereof; and a plurality of absorbent fibers, wherein said plurality of absorbent fibers is a combination of rayon fiber and superabsorbent fiber present in a percent ratio of rayon fiber to superabsorbent fiber of about 70/30, wherein said plurality of non-absorbent fibers and said plurality of absorbent fibers are blended together to form the dry expanding tampon pledget, and wherein immediately after complete ejection from an applicator, and prior to contact with menses, the dry expanding tampon pledget has a free diameter at a widest point from about 25% to about 300% larger than a diameter at said widest point of the dry expanding tampon pledget in the applicator.

10. The tampon pledget of claim 9, wherein a percent ratio of said plurality of non-absorbent fibers to said plurality of absorbent fibers is about 25/75 to about 65/35.

11. A dry expanding tampon pledget comprising:

a plurality of non-absorbent fibers, wherein said plurality of non-absorbent fibers are selected from the group consisting of polyester, polypropylene, polyethylene, aramid, nylon, acrylic, bicomponent, and any combinations thereof; and a plurality of absorbent fibers made of a combination of rayon fibers and superabsorbent fibers, wherein said plurality of non-absorbent fibers and said plurality of absorbent fibers are blended together to form the dry expanding tampon pledget, and wherein immediately after complete ejection from an applicator, and prior to contact with menses, the dry expanding tampon pledget has a free diameter at a widest point from about 25% to about 300% larger than a diameter at said widest point of the dry expanding tampon pledget in the applicator.

* * * * *